United States Patent
Holmberg et al.

(10) Patent No.: US 11,096,888 B2
(45) Date of Patent: Aug. 24, 2021

(54) LONG ACTING DRUG DELIVERY DEVICE AND ITS USE IN CONTRACEPTION

(71) Applicant: BAYER OY, Turku (FI)

(72) Inventors: Savante Holmberg, Turku (FI); Christine Talling, Turku (FI)

(73) Assignee: Bayer OY, Turku (FI)

( * ) Notice: Subject to any disclaimer, the term of this patent is extended or adjusted under 35 U.S.C. 154(b) by 0 days.

(21) Appl. No.: 15/573,187

(22) PCT Filed: May 9, 2016

(86) PCT No.: PCT/EP2016/060298
§ 371 (c)(1),
(2) Date: Nov. 10, 2017

(87) PCT Pub. No.: WO2016/180764
PCT Pub. Date: Nov. 17, 2016

(65) Prior Publication Data
US 2018/0104181 A1    Apr. 19, 2018

(30) Foreign Application Priority Data
May 13, 2015   (EP) .................................... 15167521

(51) Int. Cl.
A61K 9/00    (2006.01)
A61K 31/565    (2006.01)
A61K 31/567    (2006.01)

(52) U.S. Cl.
CPC .......... *A61K 9/0036* (2013.01); *A61K 9/0039* (2013.01); *A61K 31/565* (2013.01); *A61K 31/567* (2013.01); *A61K 9/0024* (2013.01)

(58) Field of Classification Search
CPC .. A61K 9/0036; A61K 9/0039; A61K 9/0024; A61K 31/565; A61K 31/567
See application file for complete search history.

(56) References Cited

U.S. PATENT DOCUMENTS

| | | | |
|---|---|---|---|
| 3,920,805 A | 11/1975 | Roseman | |
| 4,292,965 A | 10/1981 | Nash et al. | |
| 6,063,395 A * | 5/2000 | Markkula | A61K 9/0092 424/422 |
| 9,999,592 B2 | 6/2018 | Duesterberg et al. | |
| 2004/0247674 A1 | 12/2004 | Haapakumpu et al. | |
| 2011/0146693 A1 | 6/2011 | Duesterberg et al. | |
| 2014/0209100 A1 * | 7/2014 | Kiser | A61M 31/002 128/832 |
| 2018/0263899 A1 | 9/2018 | Duesterberg et al. | |

FOREIGN PATENT DOCUMENTS

| | | |
|---|---|---|
| EP | 0050867 A1 | 5/1982 |
| EP | 0652737 B1 | 4/1997 |
| EP | 0652738 B1 | 4/1997 |
| EP | 0876815 A1 | 11/1998 |
| EP | 1427390 A1 | 6/2004 |
| EP | 2062568 A1 | 5/2009 |
| EP | 2313084 A1 | 4/2011 |
| WO | 97/02015 A1 | 1/1997 |
| WO | 03/017971 A1 | 3/2003 |
| WO | 2004/096151 A2 | 11/2004 |
| WO | WO 2004/0961251 * | 11/2004 |

OTHER PUBLICATIONS

Merriam-Webster Dictionary, "implant", obtained online on Dec. 18, 2020. (Year: 2020).*
Brache, Vivian et al., "Current status of contraceptive vaginal rings", Contraception, Mar. 2013, pp. 264-272, vol. 87, No. 3.
Harwood, Bryna et al., "Contraceptive Vaginal Rings", Seminars in Reproductive Medicine, Dec. 2001, pp. 381-390, vol. 19, No. 4.
Mishell, Daniel R. et al., "Contraceptive effect of varying dosages of progestogen in silastic vaginal rings", Feb. 1970, pp. 99-103, vol. 21, No. 2.
International Search Report of International Patent Application No. PCT/EP2016/060298 filed Jun. 10, 2016.

* cited by examiner

*Primary Examiner* — Genevieve S Alley
(74) *Attorney, Agent, or Firm* — McBee Moore & Vanik IP, LLC

(57) ABSTRACT

The invention relates to a method for altering the release characteristics of a long acting drug delivery device containing at least two drugs in different segments, wherein the segments are arranged to a specific sequence. The invention furthermore relates to a drug delivery device with reduced initial burst containing two different drugs in different segments. The invention further relates to a delivery device manufactured according to the a.m. method and its use in contraception and gynecological therapies.

12 Claims, 4 Drawing Sheets

Figure 1:
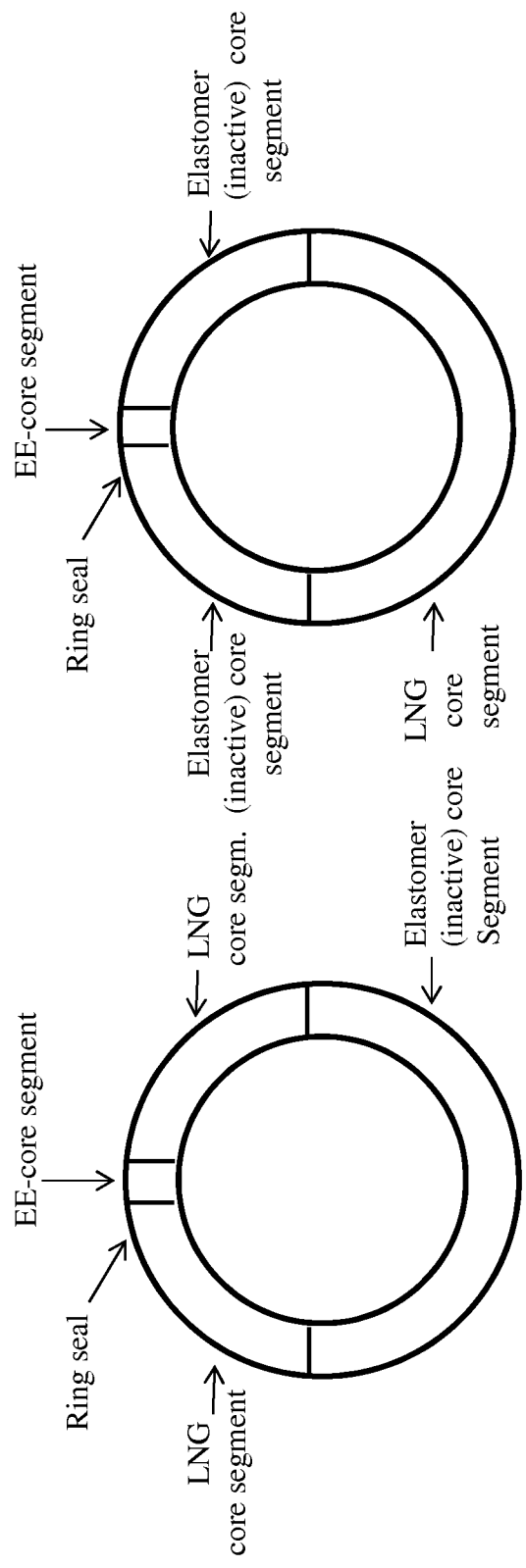

Figure 1 Ring structures
a) LNG/EE/LNG/PDMS
b) PDMS/EE/PDMS/LNG

Release rate of Ethinylestradiol [µg/day] in dependency of time [days] and temperature and storing time [0 mth vs. 2 mths]

LNG-core/EE-core/LNG-core assembly (blue diamond and green triangle curves) in comparison to Elastomer-(inactive) core/EE-core/Elastomer-(inactive) core assembly (red squares and violet cross curves)

Release rate of an intravaginal ring with LNG-core segment/EE + LNG-core segment/LNG-core segment assembly

LONG ACTING DRUG DELIVERY DEVICE AND ITS USE IN CONTRACEPTION

This application is the U.S. national phase of International Application No. PCT/EP2016/060298 filed May 9, 2016 which designated the U.S. and claims priority to EP Patent Application No. 15167521.2 filed May 13, 2015, the entire contents of each of which are hereby incorporated by reference.

The present invention relates to the subject matter as characterized in the patent claims, namely to a long acting drug delivery device containing two different pharmaceutically active drugs (A) and (B) with an reduced "burst" in the initial phase of the wearing period.

The invention further relates a process for manufacturing such a long acting drug delivery device with an reduced initial "burst", a method for altering the release characteristics of a long acting drug delivery device containing two pharmaceutically active drugs (A) and (B) and the use of such a drug delivery device in contraception and gynecological therapies.

INTRODUCTION

Hormonal contraceptives are widely accepted by users owing to easy application and high contraceptive reliability. Amongst them oral contraception (pill) is the most frequently used contraceptive method in many countries. However, there is a demand for the development of new, long-acting reversible contraceptives (LARC) that require minimal medical guidance and patient compliance compared to oral contraceptives. New LARCs like intrauterine devices (IUD) (e.g. Mirena®; EP 0652738 B1 and EP 0652737 B1) or subcutaneously placed polymer-based implants (e.g. Norplant®, Jadelle®) require less patient compliance compared to oral contraceptives.

Intravaginal rings (IVRs), such as Nuvaring®, are further widely accepted long-acting contraceptive method, as the vaginal rings can be inserted into the vagina by the user herself and is thus less invasive in comparison to implants.

The terms intravaginal ring, vaginal ring, and IVR are used synonymously in the context of this application. An intravaginal ring is a substantially ring-shaped polymeric dosage form, which provides controlled release of active ingredient(s) to the vagina over extended periods of time in which absorption of the drugs takes place via circumvention of the gastrointestinal tract.

The application in an IVR provides a convenient formulation with low variability in drug release rate, avoiding hepatic first-pass metabolism of the drug substance and improving treatment compliance since no daily (regular) recall of drug intake is required.

Rings provide a continuous release of the active ingredient(s) over a period from several weeks up to one year.

Intravaginal rings have been under clinical investigation over the last 45 years. Such intravaginal rings are devices made of flexible and drug-permeable polymers (in the context of this invention also named as matrix or core material) such as Ethinylvinylacetate (EVA) or silicone elastomers that contains the active drugs release the active drug(s) from the polymer matrix material to the vaginal mucosa for a certain period of time at a defined rate [for details see e.g. Brache et al. Contraception 2013; 87: 264-273; Harwood et al. Semin Reprod Med 2001; 19: 381-390)].

The first studies on an IVR releasing medroxyprogesterone acetate (MPA) were published by Mishell and Lumkin already in 1970 [Mishell and Lumkin. Fertil Steril 1970; 21: 99-103]. Since then, several clinical trials with IVR releasing different progestins such as progesterone, nestorone, levonorgestrel and other progestins were published.

Intravaginal rings are also described in several patents like EP 0 050 867, U.S. Pat. Nos. 3,920,805A and 4,292,965. Some IVR's described in the literature comprise a polymer matrix but no membrane or wall encasing said matrix (monolithic dosage form).

Although intravaginal rings without a membrane are described in the literature, most vaginal rings (incl. Nuvaring®) but also implants (such as Norplant®[1]) are enclosed in a membrane (also called outer layer), as the membrane ensures a more constant drug release from the polymer core segments during the wearing time.

[1] As Norplant contains as active ingredient only Levonorgestrel, which is poorly soluble in the membrane material, the initial burst is not a relevant issue here.

An IVR releasing a combination of ethinylestradiol and etonogestrel (NuvaRing®; EP00876815) was developed by Organon and introduced into the market in the early 1990s. Nuvaring® matrix consist of Ethinylvinylacetate (EVA), which is covered with a very thin membrane (here also the term "skin" is used in the literature) which is essentially composed also from EVA. In Nuvaring® both active ingredients are mixed and equally distributed over the entire ring (matrix). Thus no different core segments containing the individual drugs exist in Nuvaring®.

Intrauterine devices (also called intrauterine systems; IUS) containing at least two different drugs are described in the European patent application no. EP 13397533.4, EP2313084 and EP1427390. However, in these applications the active drugs are contained in different segments (reservoirs) which are either separated by an open space (e.g. by mounting the reservoirs in different places of the T-frame of the IUD) or by an separation membrane. Thus no diffusion from drug A from segment (reservoir) A' into segment B' (and vice versa) is possible here.

In the context of this invention it should be noted that the letter A (B) is used for the drug, whereby the letter A' (B') is used for the core segment, containing drug A or B.

Although, all long acting contraceptive methods, incl. IVR's are fully developed and well accepted in the market, they have to deal with a common problem, which is a constant drug release over the whole wearing period in particular in the initial phase of the wearing period, where an increased drug release (so called "burst effect") is observed. This leads to an unreasonable burden with the active agent for the patient. Whereby the problem is negligible with regards to drugs poorly soluble in the polymer membrane material, it is a relevant issue for drugs with an increased solubility in the membrane material.

Thus the membrane material not only regulates the drug release over the wearing period but acts also as kind of depot. Here the drug diffuses from the core material into the membrane and concentrates in the membrane during storage and transportation period.

The "accumulated drug" is emitted from the membrane, in particular during the first 1 to 3 days after insertion, which leads to a higher drug release (so called "initial burst" effect). In some cases this initial burst can last up to 7 days.

To counteract drug accumulation in the membrane it is therefore required that Nuvaring® is stored at temperatures from 2-8° C. prior dispensing it to the user (see package insert of Nuvaring® under "Storage"). But also for the end user storage in warm climate zones in a fridge is advisable and the maximal storage time at 25° C. should not exceed 4 month.

As storing and transportation at lower temperatures implies an additional efforts to the manufacturer and pharmacies, there is a need to find an alternative long acting drug delivery systems and intravaginal rings, which allows a storage at ambient temperature without resulting in an increased "burst rate" in the initial phase of the wearing period.

When using the term "initial burst" in the context of this application the drug release up to 7 days after insertion is meant. The "initial burst" is particularly pronounced on the first day after insertion of the device and declines over a time period up to 7 days till an essentially constant (steady state) release is reached. The length of this initial burst phase is dependent on the polymers used for core segments and membrane, the design (e.g. membrane thickness) of the drug delivery device, and the physic chemical properties of the drug. Thus in the context of this invention the term "initial release" means an increased release before a steady state (an essentially constant) release is reached.

OBJECT OF THE INVENTION

It is therefore an object of the invention to provide a long acting drug delivery device containing two pharmaceutically active drugs (A) and (B) with an improved release profile, namely with a reduced "initial burst" and an essentially constant drug release over the whole wearing period independent from storing conditions.

It is a further object of the invention to provide a manufacturing process for such a long acting drug delivery device with an improved release profile containing two pharmaceutically active drugs (A) and (B).

A further object of the invention is a method for altering the release characteristics of a long acting drug delivery device containing two active drugs (A) and (B).

The term "release characteristic" in the context of the present invention, refers to the release profile of the drug(s) in the initial phase after insertion of the device.

A further object of the invention is the use of such drug delivery devices with an improved release profile in contraception and gynecological therapies, in particular in the treatment of endometriosis.

BACKGROUND INFORMATION

In long acting drug delivery device with more than one active drug, in principle different device designs/structures are possible. Thus it is one option that the different drugs are contained in the polymer core matrix as a drug mixture as it is the case in Nuvaring®, where the drugs (etonogestrel and ethinylestradiol) are equally (homogeneously) distributed over the entire polymer matrix (core area) of the vaginal ring. However, (although working for the specific drug/polymer combination in Nuvaring) this results typically in a too high drug release, as the drug release is linear to the surface area[2]. Therefore, in intravaginal rings usually inactive segments, produced to from the same polymer matrix material but containing no drug(s), are added.

[2]The following formula applies with regard to the drug release: $Q=k[C_p] \times D \times A/W$ Q=drug release; $C_p$=concentration; D=diffusion rate; A=surface area; W=wall thickness Contrary to Nuvaring® (where both drugs are equally distributed over the polymer matrix), in most vaginal rings described in the literature, the different drugs (A) and (B) are located in different (matrix) segments, which are connect to form the drug delivery device.

If two different drugs are contained in different matrix segments, the matrix segments can be assembled in different sequences, e.g. in a simple AB order.

Beside a simple A/B design also more complex designs, such as an A/B/A or B/A/B sequence is possible. In this design the drug B respectively A is surrounded by two A (B) containing segments.

If the long acting drug delivery device is an intravaginal ring, normally inactive segments are added to the device. The inactive segments (subsequently called also "inert segment" or "spacer segment") are usually made of the same polymer matrix material but contain no drug. One purpose of the inactive segment is to achieve a sufficient ring size, which is needed to anchor the IVR ring reliable in the vagina of the user.

As described below in more detail, it could be a further purpose of the inert segment, to provide a spatial separation between the drug containing segments, to create a barrier between the drug containing segments. The inactive segment is preferably made of the same material as the adjoining drug containing segments.

In particular IVR systems without a membrane a further purpose of the inactive segments could be to adjust the released dose, as the released dose is dependent on the surface area of the respective segment. Contrary to this in membrane containing systems beside the surface area (of the membrane) the release can be also influence by the physic chemical properties of the membrane.

it goes without saying that the addition of an inactive segment, extends the number of variations with respect to the order of the segments, e.g. in an IVR the order of the segments could be (1) inactive segment, (2) followed by segment A', (3) followed by segment B', (4) followed by segment A' connected to inactive segment (1).

A further sequence could be (1) inactive/(2) drug A/(3) inactive/(4) drug B/connected to inactive segment (1). Many other arrangements are possible in principle, thus the a.m. sequences just serve to illustrate possible structures.

DESCRIPTION OF INVENTION

It has been found that the sequence of the segments has surprisingly an influence on the drug release, particular in the initial phase after the insertion of the long acting drug delivery device.

Thus the problem of invention (reduction of initial burst) is solved by arranging the different segments in a specific sequence/order.

It has been found that the drug release of a long acting drug delivery device in the initial phase after insertion is improved in terms of a lower initial release, when compound (B) with the better solubility in the respective matrix polymer is placed between two segments containing drug (A) which is less soluble in the matrix polymer compared to compound (B).

Even better results with in terms of the "initial burst" are obtained, if the segment containing the drug (B) with a better solubility in the polymer matrix material (encased between the two segments containing the lower soluble drug (A), contain the lower soluble drug (A) in addition to drug (B), whereby the ratio between the inferior soluble drug (A) and the better soluble drug (B) in the segment (AB') containing both drugs is in the range of 5/95 to 30/70.

With respect to intravaginal rings it is required to add an inactive segment, which contains no drug and is usually made of the same polymer material as the surrounding segments containing drug (A), (B) or (AB). This inactive segments is located between the two A' segments and connects the two A' segments to form a ring. The inactive segment causes a spatial separation of the two core segments containing drug (A). Without such an inactive core segment due to the ring shape an A/B/A sequence would practically result in an A/B sequence.

The aforesaid sequencing regarding intravaginal rings, basically applies also to inserts which are subcutaneously implanted, respectively to intrauterine devices, if these devices contain two different drugs. Although possible in theory inactive segments are not needed in the case of an intrauterine device (IUD) or implant as the inert segment would not add an additional benefit to the device.

Manufacturing and assembly of the ring segments can be done in accordance with standard techniques described in the art, e.g. EP 652738, U.S. Pat. Nos. 3,920,805, 4,888,074, 4,215,691 or WO2010/058070. However, to obtain an IVR with a reduced initial burst, it goes without saying that the correct assembly of the different segments, according to the teaching of this invention, has to be factored in, when using the manufacturing methods described in the literature.

Long acting delivery devices with reduced initial burst according to the invention are manufactured by a two-step process. In the first step (i) individual core segments in the required length of a polymer matrix material, containing either the active drug (A), or the active drug (B) respectively a drug mixture of drug (A) and (B), are prepared. In step (ii) the primed segments A', B' or AB' are assembled in the order A/B/A or A/AB/A, wherein the drug (B) is better soluble in the selected polymer matrix than drug (A).

If the long acting drug delivery system is an IVR, an inactive segment containing no drug is added to the assembly step (ii) and the "open end" of the inactive segment is combined with the "open end" of the segment containing drug (A) to form a ring with the sequence A/B/A/inactive or A/AB/A/inactive. The design and manufacture of an exemplary IVR's is described in the examples.

The invention furthermore refers to a method for altering the release characteristic of a long acting drug delivery system containing two pharmaceutically active drugs.

The method comprises preparing the drug delivery device by a process comprising the steps of:
(i) making individual core segments of a polymer matrix material, wherein the individual core segments contain either the active drug (A), the active drug (B) or a drug mixture of drug (A) and (B) for preparing a drug delivery device having reduced initial release and
(ii) assembling the individual core segments in the order A/B/A or A/AB/A,
wherein the drug B is better soluble in the selected polymer matrix than drug A.

If the drug delivery device is an intravaginal ring an inactive segment containing no drug is added to this method, which connects the two segments A' to form an IVR with the sequence A/B/A/inactive or A/AB/A/inactive.

A large variety of drugs can be used in the context of the current invention. Thus pharmaceuticals for the treatment of female diseases and contraceptive active agents are eligible, whereby progestins and estrogens are preferred in contraception and aromatase inhibitors and non-steroidal anti-inflammatory drugs (NSAID) are preferred in therapy.

Thus the invention refers also to the use of a long acting drug delivery device containing two different drugs with an improved initial release rate in contraception and therapy.

As progestins, chlormadinone acetate (CMA), norgestimate (NGM), norelgestromin (NGMN), norethisterone (NET)/norethisterone acetate (NETA), etonogestrel (3-keto-desogestrel), nomegestrol acetate (NOMAc), demegestone, promegestone, drospirenone (DRSP), medroxyprogesterone acetate (MPA), cyproterone acetate (CPA), trimegestone (TMG), levonorgestrel (LNG), norgestrel (NG), desogestrel (DSG), gestodene (GSD) or dienogest (DNG), of which levonorgestrel (LNG), desogestrel (DSG), gestodene (GSD) and dienogest (DNG) are preferred. Particular preferred is levonorgestrel.

As estrogens natural and synthetic estrogens are possible, especially estradiol or its esters, for example estradiol valerate or else conjugated estrogens (CEEs=conjugated equine estrogens) are preferred. Particularly preferred are ethinylestradiol and estrogen or their esters such as estradiol valerate or benzoate.

As aromatase inhibitor selective aromatase inhibitors such as anastrozole (Arimidex®), exemestane (Aromasin), fadrozole (Afema®), formestane (Lentaron®), letrozole (Femara®), pentrozole, vorozole (Rivizor®) and pharmaceutical acceptable salts of aromatase inhibitors are suitable, whereby anastrozole (AI) is preferred.

As NSAID non-selective Cox inhibitors, as well as selective Cox 2 inhibitors are equally suitable in the context of this invention. Preferred are meloxicam, piroxicam, naproxen, celecoxib, diclofenac, tenoxicam, nimesulide, lornoxicam and indomethacin, of which indomethacin is particularly preferred.

Depending on the selected drug the concentration of the drug in the polymer matrix is 5 to 40%, wherein a range of 10-30% is preferred.

To set the right sequencing of the drug containing segments, it is firstly required to determine the solubility of the selected drugs (A) and (B) in the respective matrix polymer.

In this context it has to be noted that solubility of the drug is not only depending on the physico-chemical properties of the selected drug but also on the selected matrix polymer. For silicone-elastomer based matrix as a rule of thumb, hydrophobic drugs are better soluble than hydrophilic drugs.

In principle it is also possible in the context of this invention to use different polymer matrix material (in dependency from the drug) for the different segments. However, it is advantageous if the core matrix material is the same for all segments (incl. the inactive segment).

However, in the context of the present invention the specific solubility of the selected drug in the respective polymer is of no importance. It is rather important that there is a difference in the solubility between drug (A) and (B) and that the segment with the substance with better solubility B is always located between two segments of the inferior soluble substance A. It is particular preferred, if the segment with the better soluble drug B contains in addition also drug A in a range of 5 to 30 ww % (relating to the segment containing the drug mixture A and B).

The solubility of drugs (API=active pharmaceutical ingredient) in different polymers can be determined as follows:
(a) Solubility of API in Polysiloxanes The polysiloxane (polyethylene oxide block-polydimethylsiloxane copolymer, poly(3,3,3-trifluoropropylmethylsiloxane, or poly(dimethylsiloxane) used for measuring solubility of API should have a low viscosity, ca. 1000 cSt ($mm^2$/s).

Weigh 15-20 mg API and add to a centrifuge tube containing 10 ml polysiloxane, stir on magnetic stirrer for 3 days. Add API if needed. Separate undissolved API by centrifuge. Take an aliquot of the clear solution or filter the aliquot with a syringe. 0.2 g of the solution is added to a 5.0-ml volumetric flask, filled with THF (Tetrahydrofuran) and mixed well. Depending on the solubility of API, analyze sample solution by HPLC as is or diluted.

(b) Solubility of API in Thermoplastic Polymer

The solubility of API's in thermoplastic polymers is measured according to standard methods as described by A. Mahieu in Mol Pharm 2013, 10, 560-566, R. A. Bellantone et al in J Pharm Sci 2012, 101, 4549-4558, Y. Sun et al. in J Pharm Sci 2012, 99, 4023-4031 or P. Marsac et al. in Pharm Res 2006, 23, 2417-2426.

The drug delivery devices of the current invention are usually covered with a polymer based membrane. The membrane is brought up to the core segment according to known methods, e.g. by swelling of the membrane in cyclohexane and removal of the solvent after insertion of the core segments. Also pressurized air or vacuum can be applied to expand the membrane prior insertion of the core segments. Respective methods are described e.g. in EP 065273881 B1.

The membrane material could be the same of different from the core segment material, whereby it is preferred in the context of this invention, if the materials are different and the solubility of the drug in the matrix (core segment) is higher as in the membrane. Different means not necessarily that the membrane polymer is selected from a different compound class, it is rather sufficient if the selected polymer is modified by adding e.g. functional groups such as 3,3,3-trifluoropropylmethylgroups, to a silicon elastomer change the hydrophobicity of the material. Solubility of drugs in various polymers can be determined as described above.

As matrix/core segment material thermoplastic polymers such as EVA (Ethinyl-Vinyl-Acetate) or elastomeric silicones, such as polysiloxanes are suitable.

Such materials can also be used as membrane material in the context of the present invention. Polysiloxanes are regulating the permeation rate of drugs. They are physiologically inert, and a wide group of therapeutically active substances are capable of penetrating polysiloxane membranes. Furthermore siloxanes have also the required strength properties.

Poly(disubstituted) siloxanes where the substituents are lower alkyl, preferably alkyl groups of 1 to 6 carbon atoms, or phenyl groups, wherein said alkyl or phenyl can be substituted or unsubstituted, are preferred as core segments and membrane material. A widely used and preferred polymer of this kind is poly(dimethylsiloxane) (PDMS). Other preferred polymers are siloxane-based polymers comprising either 3,3,3 trifluoropropyl groups attached to the silicon atoms of the siloxane units (fluoro-modified polysiloxanes) or poly(alkylene oxide) groups, wherein said poly(alkylene oxide) groups are present as alkoxy-terminated grafts or blocks linked to the polysiloxane units by silicon-carbon bonds or a mixture of these forms. Polysiloxanes and modified polysiloxane polymers are described for example in EP 0652738 B1, WO 00/29464 and WO 00/00550. Among siloxane-based polymers comprising poly(alkylene oxide) groups, polyethylene oxide block-polydimethylsiloxane copolymer (PEO-b-PDMS) are preferred.

Polysiloxanes without substituents are unipolar polymers and thus hydrophilic drugs are poorly soluble in such siloxane elastomers. However, the solubility of hydrophilic API's can be enhanced, if polar groups, such as poly(alkylene oxide) groups are present in the siloxane. Thus unipolar polymers are used for hydrophobic drugs, whereby polar siloxanes are preferred for hydrophilic drugs.

A preferred embodiment of the invention refers to a polysiloxane based contraceptive ring containing Levonorgestrel (LNG) and Ethinylestradiol (EE), wherein in this drug combination EE is the drug with the higher solubility and thus the order of the segments is (1) inactive, (2) LNG, (3) EE, (4) LNG connected to the inactive material segment (1) to form a ring.

It is particular preferred it the EE segment (3) contains Levonorgestrel in addition. Here the ratio between LNG/EE/ in segment (3), containing the drug mixture, is 5/95 to 30/70 w/w %.

A further preferred embodiment of the invention refers to an Anastrozol and Levonorgestrel containing silicon elastomer based IVR, wherein the Levonorgestrel containing segment (B') is located between two Anastrozole containing segments (A'), as in this combination Anastrozole is the drug with the lower solubility in a silicon elastomer. It is particular preferred if the Levonorgestrel segment, contains Anastrozole in addition, whereby the ratio of the Anastrozole to LNG in the segment containing the drug mixture is from 5/95 to 40/60 w/w %.

The IVR of the invention can be continuously used for approximately one month up to one year, preferably for one to six months. Continuous use includes that the IVR can be taken out intermittently for 1 up to 4 hours for e.g. cleaning or during intercourse. Alternatively according to the invention the IVR can be used in such a way that it will mimic the natural cycle of the woman (e.g. for 21, 22, 23 or 24 days or up to a month), subsequently removed to initiate the bleeding and is re-inserted after 7, 6, 5, 4 or 3 days (wearing days and non-wearing days should sum up to at least 28 days). Alternatively a new unused IVR can be inserted after this time.

The release of a drug from the delivery device in particular an IVR is described by the release rate. Release rate means the average amount of active drug substance released from the device within 24 hours that is available for absorption by the surrounding tissue.

The polymer composition of the core segments and/or the membrane, membrane thickness, and membrane surface area are the main parameters which influence the release rate. In-vitro release rate test is routinely used in the art to characterize hormone-containing delivery devices such as IVRs. In this test the release rate is determined by analyzing the released amount of a drug in vitro at 37° C., e.g. in an aqueous solution of cyclodextrin in a shaking water bath for the intended time of use of the device in vivo. The in vitro release rate at each sampling time point is calculated as released amount (pig) per day (24 h) [μg/day or μg/d]. The term dose and release rate are used synonymously in this patent application.

The subsequent examples serve to illustrate the invention.

Example 1 a) refers to a ring with a segment sequence LNG/EE/LNG/inactive. The inactive or inert material in this example is PDMS elastomer. For comparison purposes a vaginal ring with the sequence Inactive/EE/inactive/LNG has been prepared (example 1 b). The respective ring structures are shown in FIG. 1 (LNG/EE/LNG/PDMS left; PDMS/EE/PDMS/LNG right).

In Table 1 of example 1 the dimensions of the different segments are given. Table 2 refers to the release rates of EE measured for the different assemblies, LNG/EE/LNG/inactive according to the invention and inactive/EE/inactive/LNG according to the State of the Art. The release rates have been measured as described above in an in-vitro test at 37° C. in an aqueous solution of cyclodextrin.

Figure 2:
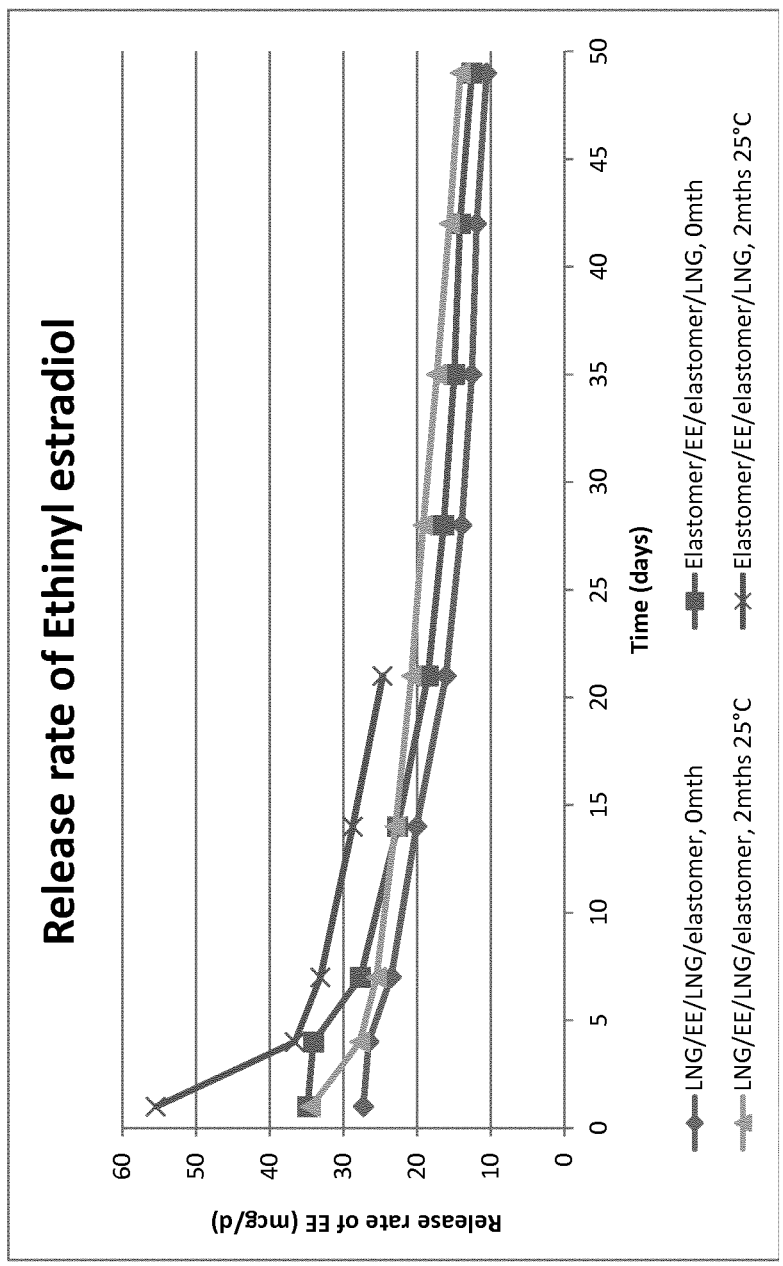

The release rates of EE in dependency from time (days) as given in Table 1 are also plotted in an arithmetic chart (see FIG. 2). The highest initial burst is observed for the comparator assembly elastomer(inactive)/EE/elastomer(inactive)/LNG after 2 month storing time at 25° C. Here in the initial burst phase the release is above 55 μg on day one (violet cross curve). The figures also clearly indicate the accumulation of the EE in the membrane in dependency of the storing time as for an identical assembly after 0 month storing time the initial release is 35 μg only (red square curve).

Contrary to this for an assembly according to the invention LNG/EE/LNG elastomer (inactive) the release rate at day one after 0 month storing time is 27 μg only (blue diamond curve) and only a slight increase is observed after 2 month storing time at 25° C. A value of 35 μg was observed at day 1 (green triangle curve).

Figure 3:
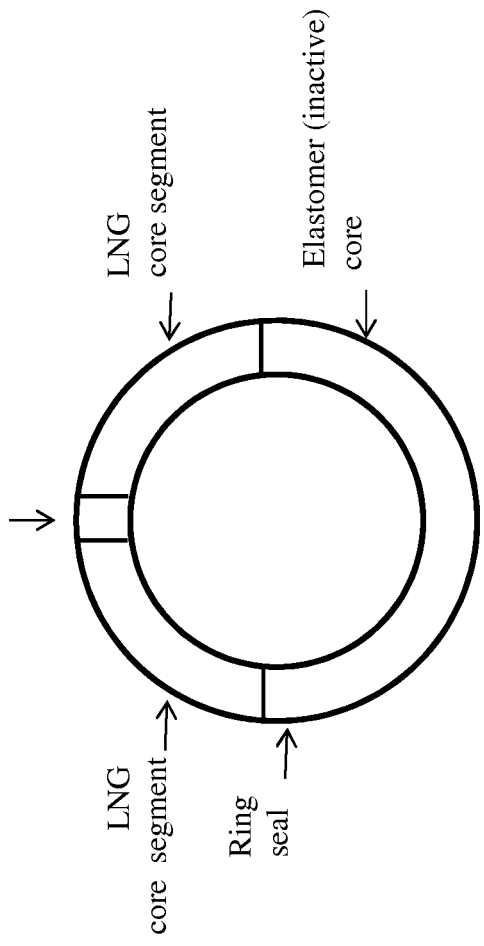
Figure 4:
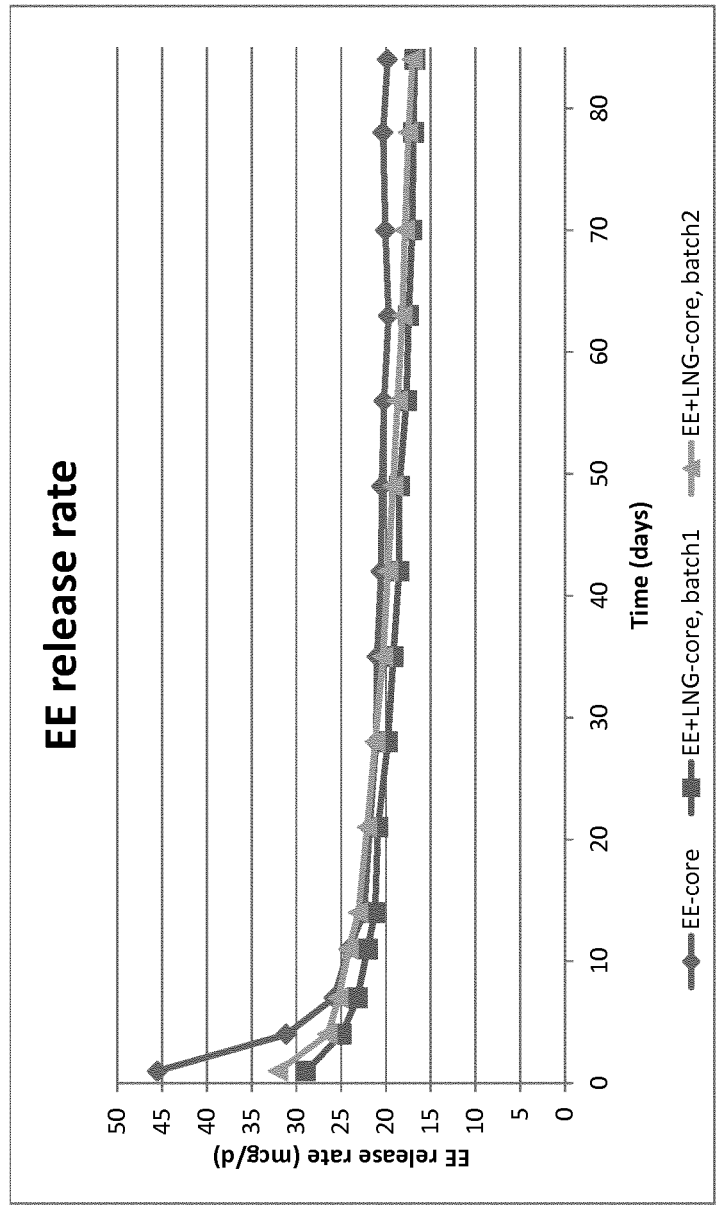

Example 2 refers to a LNG/EE plus LNG/LNG/PDMS assembly according to the invention (PDMS segment=inactive segment) which is compared to an LNG/EE/LNG/PDMS assembly according to a second embodiment of the invention. This comparison shows that a further improvement in terms of reduction of the "initial bust" can be achieved, if the EE segment (B) contains LNG in addition. The ring structure is shown in FIG. 3. Dimensions of the segments are given in Table 3. The release rates have been measured as described above and are given in Table 3. EE release over the time is plotted in FIG. 4. As it can be seen from the data and FIG. 4 the "initial burst" is further reduced when adding LNG to the EE containing segment. Thus the EE release on the first day is reduced from ~45 μg (blue "diamond" curve) on day 1 to ~30 μg on day one (green triangle respectively red square curves).

Example 1

Manufacturing of EE- and LNG-Releasing Rings
Core
Three core compositions were prepared, one inert core, one EE comprising core and on LNG comprising core. The matrices of the EE- and the LNG-comprising cores were made of silicone elastomer (polydimethylsiloxane), and the inert core was also made of silicone elastomer (polydimethylsiloxane). The EE-containing core was produced by mixing micronized EE and the silicone elastomer in a mixer. The EE content of the mixture was 10% by weight. The mixture was shaped in molds and cured to give small discs having the outer diameter of about 4.5 mm. The LNG-containing core was produced by mixing micronized LNG and the silicone elastomer in a mixer. The LNG content of the mixture was 50% by weight. The LNG-core was extruded into a tubing with an inner diameter of about 2.0 mm and an outer diameter of about 4.5 mm. The inert silicone elastomer core was also extruded to give an elastic tubing with an inner diameter of about 1.4 mm and an outer diameter of about 4.5 mm.
Membrane
The drug-release-controlling membrane tubing was produced by extrusion. The membrane was made of silicone elastomer (polydimethylsiloxane). The inner diameter of the membrane tubing was about 4.3 mm and the outer diameter about 5.0 mm.
Assembly of the Ring
a) LNG/EE/LNG/PDMS
The LNG core was cut into two 37 mm pieces (subsequently also named as core segments). To fill out the whole ring a PDMS core tubing was used in the ring core as an inert segment. The inert PDMS elastomer core was cut into 80 mm length so that a total core length of 157 mm was achieved. The membrane tubing was cut to a length of 165 mm and swollen in cyclohexane. The ring was put together by pushing the core segments into the swollen membrane tubing in the following order: first LNG-core segment, elastomer-core segment, second LNG-core segment, and EE-core segment. The tubing was shaped into a ring by overlapping and gluing. For closing the ring joint, a small amount of a PDMS glue was used. After evaporation of the solvents, the tubing contracted and compressed the parts tightly.

b) PDMS/EE/PDMS/LNG (Comparison Example)
The LNG core was cut into 74 mm pieces (core segment). To fill out the whole ring a PDMS core tubing was used in the ring core as an inert segment. The inert PDMS elastomer core was cut into two 40 mm pieces resulting in a total core length of 157 mm (core segment). The membrane tubing was cut to a length of 165 mm and swollen in cyclohexane. The ring was put together by pushing the core segments into the swollen membrane tubing in the following order: first elastomer-core-, LNG-core-, second elastomer-core-, and EE-core-segment. The tubing was shaped into a ring by overlapping and gluing. For closing the ring joint, a small amount of a PDMS glue was used. After evaporation of the solvents, the tubing contracted and compressed the parts tightly. Ring structures are shown in FIG. 1, dimensions of the different segments are given in Table 1 below.

TABLE 1

Properties and materials of IVR releasing Ethinylestradiol and Levonorgestrel.

| Ring component | Material | Length (mm) | OD (mm) | ID (mm) |
|---|---|---|---|---|
| Membrane tubing | Polydimethylsiloxane | 165 | 5.0 | 4.3 |
| LNG core (tubing) | Polydimethylsiloxane | 37 + 37* 74** | 4.5 | 2.0 |
| EE core | Polydimethylsiloxane | 3 | 4.5 | — |
| Elastomer core (tubing) | Polydimethylsiloxane | 80* 40 + 40** | 4.5 | 1.4 |

*Ring structure a) FIG. 1 left
**Ring structure b) FIG. 1 right
ID (inner diameter of the membrane tube);
OD (outer diameter of the membrane tube).

TABLE 2

In vitro release rate of Ethinylestradiol (EE) from IVR with different structure and storage.

| Time (days) | LNG/EE/ LNG/inact. 0 mth, (μg/d) | Elast./EE/ inact./LNG 0 mth, (μg/d) | LNG/EE/ LNG/inact. 2 mths 25° C., (μg/d) | inact./EE/ incat./LNG 2 mths 25° C., (μg/d) |
|---|---|---|---|---|
| 1 | 27.3 | 34.9 | 34.5 | 55.4 |
| 4 | 26.6 | 34.1 | 27.8 | 36.6 |
| 7 | 23.5 | 27.7 | 25.5 | 33.1 |
| 14 | 20.1 | 22.7 | 23.0 | 28.7 |
| 21 | 16.1 | 18.5 | 20.8 | 24.7 |
| 28 | 14.0 | 16.4 | 19.2 | N/A |
| 35 | 12.6 | 15.0 | 17.3 | N/A |
| 42 | 11.9 | 14.2 | 15.6 | N/A |
| 49 | 10.6 | 12.6 | 14.1 | N/A |

0 mth = no storage time, release measured immediately after manufacturing

Example 2

Manufacturing of EE- and LNG-Releasing Rings

Core

Four core compositions were prepared, one inert core, one EE comprising core, one EE+LNG comprising core, and one LNG comprising core. The matrices of the EE-, the EE+LNG, and the LNG-comprising cores were made of silicone elastomer (polydimethylsiloxane), and the inert core was also made of silicone elastomer (polydimethylsiloxane). The EE-containing core was produced by mixing micronized EE and the silicone elastomer in a mixer. The EE content of the mixture was 20% by weight. The EE+LNG-containing core was produced by mixing micronized EE, micronized LNG and the silicone elastomer in a mixer. The EE content of the mixture was 20% by weight and the LNG content was 10% by weight. The EE+elastomer and the EE+LNG+elastomer mixtures were shaped in molds and cured to give small discs having the outer diameter of about 4.5 mm. The LNG-containing core was produced by mixing micronized LNG and the silicone elastomer in a mixer. The LNG content of the mixture was 50% by weight. The LNG-core was extruded into a tubing with an inner diameter of about 2.0 mm and an outer diameter of about 4.5 mm. The inert silicone elastomer core was also extruded to give an elastic tubing with an inner diameter of about 1.4 mm and an outer diameter of about 4.5 mm.

Membrane

The drug-release-controlling membrane tubing was produced by extrusion. The membrane was made of silicone elastomer (polydimethylsiloxane). The inner diameter of the membrane tubing was about 4.3 mm and the outer diameter about 5.0 mm.

Assembly of the Ring

The LNG core was cut into two 43-46 mm pieces (core segment). To fill out the whole ring a PDMS core tubing was used in the ring core as an inert segment. The inert PDMS elastomer core was cut into 65-71 mm length (core segment) so that a total core length of 160 mm was achieved. The membrane tubing was cut to a length of 160 mm and swollen in cyclohexane. The ring was put together by pushing the core segments into the swollen membrane tubing in the following order: first LNG-core-, EE-core- or EE+LNG-core, second LNG-core, and elastomer-core-segment. The tubing was shaped into a ring by gluing. For closing the ring joint, a small amount of a PDMS glue was used. After evaporation of the solvents, the tubing contracted and compressed the parts tightly.

TABLE 3

Properties and materials of IVR releasing Ethinylestradiol and Levonorgestrel.

| Ring component | Material | Length (mm) | OD (mm) | ID (mm) |
|---|---|---|---|---|
| Membrane tubing | Polydimethylsiloxane (PDMS) | 160 | 5.0 | 4.3 |
| LNG core (tubing) | Polydimethylsiloxane (PDMS) | 43-46 + 43-46 | 4.5 | 2.0 |
| EE core or EE plus LNG | Polydimethylsiloxane (PDMS) | 3 | 4.5 | — |
| Elastomer core (tubing) | Polydimethylsiloxane (PDMS) | 65-71 | 4.5 | 1.4 |

ID (inner diameter of the membrane tube);
OD (outer diameter of the membrane tube).

TABLE 4

In vitro release rate of Ethinylestradiol from IVR with or without LNG in the EE-core

| Time (days) | EE-core (µg/d) | EE + LNG core, batch 1 (µg/d) | EE + LNG core, batch 2 (µg/d) |
|---|---|---|---|
| 1 | 45.5 | 28.9 | 32.0 |
| 4 | 31.1 | 24.9 | 26.5 |
| 7 | 25.8 | 23.2 | 25.3 |
| 11 | 24.1 | 22.1 | 24.1 |
| 14 | 22.4 | 21.2 | 23.1 |
| 21 | 21.8 | 20.9 | 22.1 |
| 28 | 21.1 | 19.8 | 21.2 |
| 35 | 21.0 | 19.2 | 20.3 |
| 42 | 20.5 | 18.5 | 19.8 |
| 49 | 20.5 | 18.5 | 19.2 |
| 56 | 20.2 | 17.7 | 18.7 |
| 63 | 19.7 | 17.5 | 18.2 |
| 70 | 20.1 | 17.1 | 17.9 |
| 78 | 20.3 | 16.9 | 17.5 |
| 84 | 19.8 | 16.8 | 17.0 |

The invention claimed is:
1. A method for altering the release characteristics of a long acting drug delivery device containing two pharmaceutically active drugs, the method comprises preparing the drug delivery device by a process comprising the steps of:
 (i) making individual core segments of a polymer matrix material, wherein the individual core segments contain either the active drug (A) or a drug mixture AB of drug (A) and active drug (B) for preparing a drug delivery device having reduced initial release and
 (ii) assembling the individual core segments in the order A/AB/A,
 wherein the drug B is more soluble in the selected polymer matrix than drug A,
 wherein the long acting drug delivery device is an implant or an IUD,
 wherein drug (B) with higher solubility is an estrogen and drug (A) with lower solubility is a progestin, and
 wherein the core segments comprise a silicone elastomer material selected from the group consisting of PDMS, a fluoro-modified polysiloxane, and a poly(alkylene oxide) modified polysiloxane, or a mixture thereof.
2. The method according to claim 1, wherein the estrogen is ethinylestradiol (EE) and wherein the progestin is levonorgestrel (LNG).
3. The method according to claim 1, wherein the ratio between progestin and the estrogen in segment AB is in the range 5/95 w/w % to 30/70 w/w %.
4. The method according to claim 1, wherein the core segments are covered with a silicone based membrane.
5. The method according to claim 4, wherein the silicone based membrane is selected from the group consisting of PDMS, a fluoro-modified polysiloxane and a poly(alkylene oxide) modified polysiloxane, or a mixture thereof.
6. The method according to claim 5, wherein the silicone based membrane is polyethylene oxide block-polydimethylsiloxane copolymer (PEO-b-PDMS).
7. The method according to claim 1, wherein only the core segment AB containing estrogen and progestin is covered with a membrane.
8. The method according to claim 7, wherein the membrane is a silicone based membrane selected from the group consisting of PDMS, a fluoro-modified polysiloxane, and a poly(alkylene oxide) modified polysiloxane, or a mixture thereof.

9. The method according to claim 1, wherein the drug delivery device reduces initial burst effect.

10. The method according to claim 1, wherein in the individual core segments, the active drug (A) or the drug mixture of drug (A) and drug (B) drug is dispersed in a solid core.

11. The method according to claim 1, wherein the poly (alkylene oxide) modified polysiloxane is polyethylene oxide block-polydimethylsiloxane copolymer (PEO-b-PDMS).

12. A process for preparing a long acting drug delivery device, whereby the drug delivery device is manufactured by a process comprising the steps of:
   (i) making individual core segments of a polymer matrix material, wherein the individual segments contain either the active drug (A), or a drug mixture AB of drug (A) and active drug (B) for preparing a drug delivery device having reduced initial release and
   (ii) assembling the individual core segments in the order A/AB/A,
   wherein the drug B is more soluble in the selected polymer matrix than drug A,
   wherein the long acting drug delivery device is an implant or an IUD,
   wherein drug (B) with higher solubility is an estrogen and drug (A) with lower solubility is a progestin, and
   wherein the core segments comprise a silicone elastomer material selected from the group consisting of PDMS, a fluoro-modified polysiloxane, and a poly(alkylene oxide) modified polysiloxane, or a mixture thereof.

* * * * *